(12) United States Patent
Yu et al.

(10) Patent No.: US 9,095,445 B2
(45) Date of Patent: Aug. 4, 2015

(54) VERTEBRAL INTERBODY SPACER

(75) Inventors: Kidong Yu, Memphis, TN (US); Keith E. Miller, Germantown, TN (US); William D. Armstrong, Memphis, TN (US); Charles Branch, Advance, NC (US); Kevin T. Foley, Germantown, TN (US); Peter McCombe, Brisbane (AU); Anthony J Melkent, Memphis, TN (US); William R. Sears, Warrawee Sydney (AU)

(73) Assignee: Warsaw Orthopedic, Inc., Warsaw, IN (US)

( * ) Notice: Subject to any disclaimer, the term of this patent is extended or adjusted under 35 U.S.C. 154(b) by 19 days.

(21) Appl. No.: 13/182,942

(22) Filed: Jul. 14, 2011

(65) Prior Publication Data

US 2013/0018466 A1    Jan. 17, 2013

(51) Int. Cl.
*A61F 2/44*    (2006.01)
*A61F 2/46*    (2006.01)
*A61F 2/30*    (2006.01)

(52) U.S. Cl.
CPC ............... *A61F 2/447* (2013.01); *A61F 2/4455* (2013.01); *A61F 2/4611* (2013.01); *A61F 2002/3008* (2013.01); *A61F 2002/30062* (2013.01); *A61F 2002/30266* (2013.01); *A61F 2002/30281* (2013.01); *A61F 2002/30616* (2013.01); *A61F 2002/30772* (2013.01); *A61F 2002/30774* (2013.01); *A61F 2002/30904* (2013.01); *A61F 2002/448* (2013.01); *A61F 2002/4475* (2013.01); *A61F 2002/4622* (2013.01); *A61F 2002/4627* (2013.01); *A61F 2002/4629* (2013.01); *A61F 2310/00017* (2013.01); *A61F 2310/00023* (2013.01); *A61F 2310/00131* (2013.01);

(Continued)

(58) Field of Classification Search
CPC ...... A61F 2/4455; A61F 2/4611; A61F 2/447
USPC .............. 623/17.11–17.16; 606/248, 249
See application file for complete search history.

(56) References Cited

U.S. PATENT DOCUMENTS

| 4,834,757 A | * | 5/1989 | Brantigan | .............. 623/17.11 |
| 4,863,477 A | | 9/1989 | Monson | |
| 5,425,772 A | * | 6/1995 | Brantigan | .............. 623/17.11 |

(Continued)

FOREIGN PATENT DOCUMENTS

| WO | WO 01/28465 A2 | 4/2001 |
| WO | 2004093752 A2 | 11/2004 |

OTHER PUBLICATIONS

International Search Report and Written Opinion for PCT/US2012/044181 the counterpart application mailed on Dec. 27, 2012.

*Primary Examiner* — Matthew Lawson
*Assistant Examiner* — Si Ming Lee

(57) ABSTRACT

An interbody spacer includes an elongated body with a maximum width between opposite side walls and a maximum height between upper and lower bearing surfaces. The interbody spacer also includes a leading end nose connecting the side walls to facilitate insertion of the interbody spacer into a disc space between vertebrae in an insertion orientation, from which the interbody device is then rotated to position the upper and lower bearing surfaces in contact with the endplates of the adjacent vertebrae. The leading end nose forms a blunt convex nose between the upper and lower bearing surfaces to maximize the bearing surface area available to contact the adjacent endplates.

24 Claims, 12 Drawing Sheets

(52) U.S. Cl.
CPC ................ *A61F2310/00179* (2013.01); *A61F 2310/00359* (2013.01)

(56) References Cited

U.S. PATENT DOCUMENTS

| | | | |
|---|---|---|---|
| 5,443,514 A | 8/1995 | Steffee | |
| 5,534,030 A | 7/1996 | Navarro et al. | |
| 5,653,762 A | 8/1997 | Pisharodi | |
| 5,658,336 A | 8/1997 | Pisharodi | |
| 5,716,415 A | 2/1998 | Steffee | |
| 5,766,252 A | 6/1998 | Henry et al. | |
| 5,888,224 A | 3/1999 | Beckers et al. | |
| 5,984,922 A | 11/1999 | McKay | |
| 6,030,390 A | 2/2000 | Mehdizadeh | |
| 6,080,158 A | 6/2000 | Lin | |
| 6,093,207 A | 7/2000 | Pisharodi | |
| 6,224,631 B1 | 5/2001 | Kohrs | |
| 6,245,108 B1 | 6/2001 | Biscup | |
| 6,251,140 B1 | 6/2001 | Marino et al. | |
| 6,290,724 B1 | 9/2001 | Marino | |
| 6,309,421 B1 | 10/2001 | Pisharodi | |
| 6,325,827 B1 | 12/2001 | Lin | |
| 6,368,325 B1 | 4/2002 | McKinley et al. | |
| 7,169,183 B2 | 1/2007 | Liu et al. | |
| 7,316,686 B2 * | 1/2008 | Dorchak et al. | 606/86 A |
| 7,749,270 B2 | 7/2010 | Peterman | |
| 8,343,224 B2 * | 1/2013 | Lynn et al. | 623/17.16 |
| 2004/0102847 A1 * | 5/2004 | Sato et al. | 623/17.11 |
| 2008/0119937 A1 * | 5/2008 | McCombe et al. | 623/17.16 |
| 2008/0249629 A1 | 10/2008 | Eckman | |
| 2008/0288076 A1 * | 11/2008 | Soo et al. | 623/17.16 |
| 2009/0248163 A1 * | 10/2009 | King et al. | 623/17.16 |
| 2010/0152853 A1 * | 6/2010 | Kirschman | 623/17.16 |
| 2010/0262244 A1 * | 10/2010 | Savage-Erickson et al. | 623/17.16 |
| 2011/0190889 A1 * | 8/2011 | Miller et al. | 623/17.16 |
| 2011/0295372 A1 * | 12/2011 | Peterman et al. | 623/17.16 |

\* cited by examiner

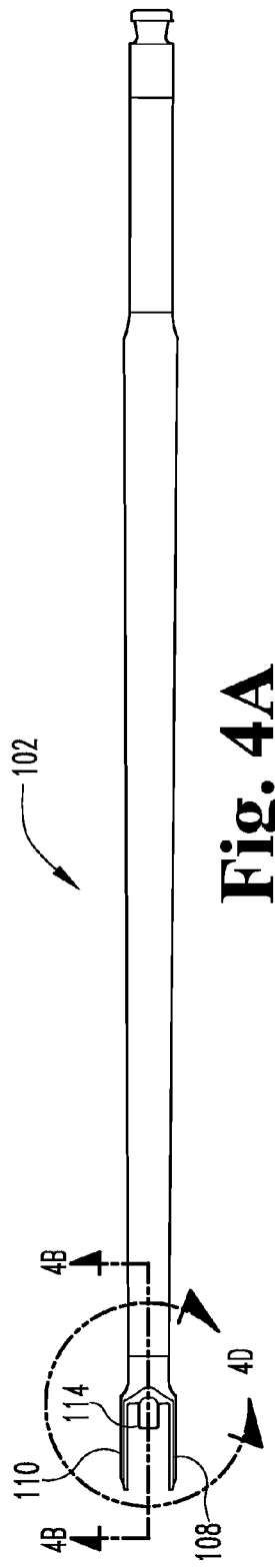
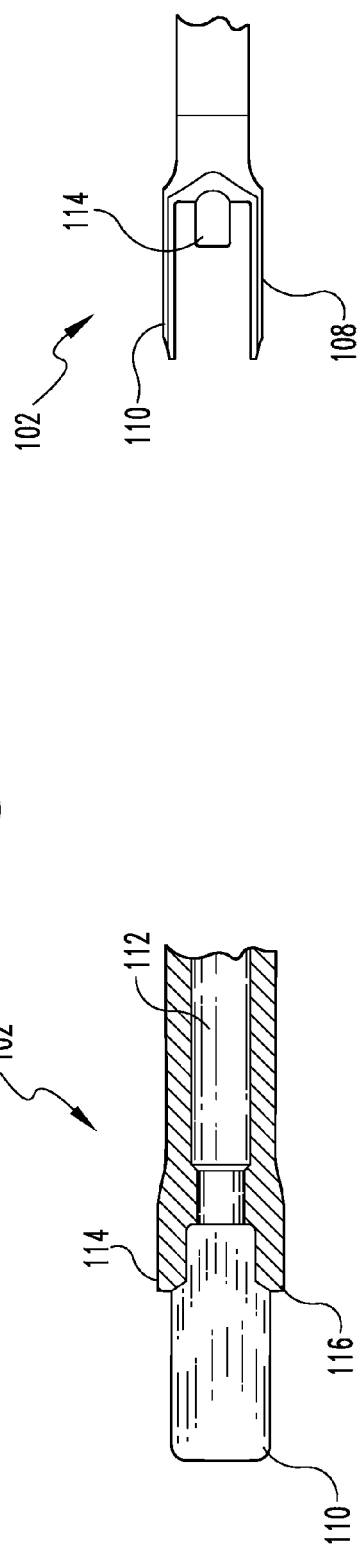
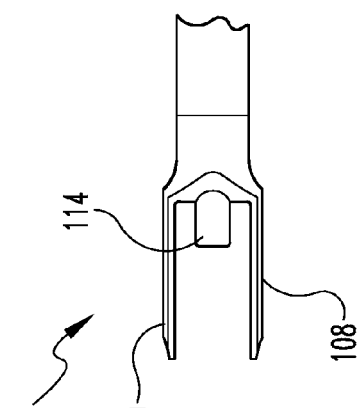
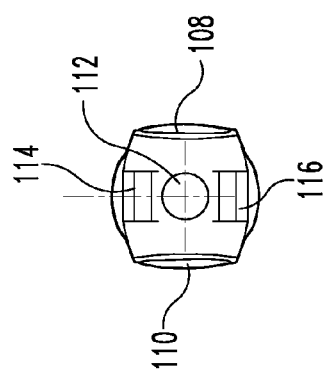
Fig. 4A
Fig. 4B
Fig. 4D
Fig. 4C

VERTEBRAL INTERBODY SPACER

BACKGROUND

The present invention relates generally to treatment of the spinal column, and more particularly relates to a vertebral interbody spacer for placement between adjacent vertebral bodies of a spine to create and maintain a desired orientation and spacing between the adjacent vertebral bodies.

It is known that if an intervertebral disc is damaged, it can be removed and the resulting space between the two adjacent vertebrae may be filled with a bone growth inducing substance to promote a boney fusion across the disc space. Fixation devices external to the disc space have been utilized to maintain the position of the adjacent vertebrae while the intervening material fuses with adjacent bone to form a boney bridge. As an alternative or in conjunction with fixation devices, load bearing spacers, such as artificial devices or bone grafts, may be placed in the empty disc space. These spacers transmit the loading from one adjacent vertebra to the other adjacent vertebra during the healing process. Further, when an intervertebral disc is damaged there is often a loss of height of the disc and a loss of the normal angle (lordosis) between the vertebra on each side of the disc. Spacers may also be used to restore the height and angle (lordosis) of a damaged intervertebral disc. Such spacers may be provided in a variety of forms.

A need exists for improvements to interbody spacers and the present invention is directed to such need.

SUMMARY

The present invention provides an improved interbody spacer adapted for spacing two adjacent vertebral bodies. The invention provides mechanisms to achieve the desired goals of distracting the intervertebral space and, when desired, of increasing the lordosis angle between the adjacent vertebral bodies. The initial increase in height is obtained by insertion of the spacer body into the disc space in one orientation whereby distraction is obtained by means of a small radius bullet shaped nose. Further increase in height and increase in lordosis is obtained by rotation of the spacer body about its longitudinal axis by, for example, a quarter turn.

Various aspects are summarized below, but it should be understood that embodiments are contemplated that incorporate any one or combination of these features, omit one or more of the following features, or include other features not specifically discussed. The interbody spacer includes an elongated body extending on a center longitudinal axis with opposite upper and lower bearing surfaces and opposite side walls that are convexly rounded along the longitudinal axis. As used herein, side walls convexly rounded along the longitudinal axis means that the side walls are curved outwardly from the longitudinal axis from a leading end portion to a trailing end of the spacer when the spacer is viewed from a direction looking orthogonally toward either its upper or lower bearing surface. The side walls diverge from the trailing end toward the leading end portion so that that spacer provides a maximum width at a location that is offset from a mid-length plane of the spacer in a direction toward the leading portion. The side walls converge from this maximum width location to the leading end portion of the spacer where the side walls define a bullet-shaped tip when viewed in a direction looking orthogonally toward one of the upper and lower bearing surfaces. The bullet-shaped tip connecting the side walls facilitates insertion of the spacer between and distraction of adjacent vertebrae when the spacer is oriented in an insertion orientation in which the side walls are positioned to face the endplates of the vertebrae. When viewed from a direction looking on the longitudinal axis of the interbody spacer toward either the leading end portion or the trailing end of the spacer, the side walls are linear from the upper bearing surface to the lower bearing surface. The leading end portion forms a blunt, convexly rounded nose extending between the upper and lower bearing surfaces that is substantially larger than the bullet-shaped tip in the transverse direction so that the length of the upper and lower bearing surfaces along the longitudinal axis available to contact the endplates is maximized. In one embodiment the complex rounded nose in the transverse direction includes a complex curve with at least two different radii from the nose to the adjacent side wall. This complex curve allows the leading end of the spacer body to have a small radius that transitions to a larger radius before intersecting the upper and lower bearing surfaces. The smaller radius curvature enhances the ability of the leading edge to distract the narrowed disc space on initial insertion while the larger radius maintains the point of intersection with the upper and lower surface at a position such that sufficient surface area of the upper and lower bearing surfaces is maintained. The upper and lower bearing surfaces define a height of the spacer and are convexly rounded along the longitudinal axis from the leading end portion to the trailing end of the spacer. The upper and lower bearing surfaces define a maximum height at a second location that is offset from the mid-length plane of the spacer toward the leading end portion of the spacer. The side walls also each define an elongated slot extending from the trailing end toward the leading end portion. The slots diverge from one another in a direction toward the leading end portion and are configured to receive an inserter instrument therein. The trailing end includes a receptacle between the slots to receive the inserter instrument. The interbody spacer also includes a central cavity that extends through the upper and lower bearing surfaces. The slots each include at least one hole that opens into the cavity. The upper and lower bearing surfaces also include elongated projections that extend between the side walls orthogonally to the longitudinal axis of the spacer.

The present invention also provides an inserter instrument for use in combination with an interbody spacer. According to one aspect, the inserter has a gripping end with fingers that are wedged into diverging slots formed along opposite side walls of the interbody spacer when a holding member of the inserter is engaged to a trailing end of the interbody spacer.

The present invention also provides a method for inserting an improved interbody spacer. In one aspect of the method and the spacer, the inserter is oriented so that the spacer is positioned with its side walls facing respective ones of the adjacent endplates the vertebrae, and then the spacer is inserted into the disc space so that its bullet-shaped nose leads its entry into the disc space and the longitudinal convexly rounded side walls separate the adjacent vertebrae. The spacer is then rotated in situ to further distract the vertebrae as its upper and lower bearing surfaces are positioned in contact with the endplates of the adjacent vertebrae. In one aspect, the spacer includes transverse projections extending across the upper and lower bearing surfaces. In a direction between the side walls, the ends of the transverse projections lie on an arc defined by a first radius that is substantially smaller than a second arc defined by a second radius on which the upper and lower bearing surfaces lie. The increased curvature of the ridges facilitates in situ rotation of the spacer about its longitudinal axis and the smaller curvature of the upper and lower bearing surfaces provides increases stability for the spacer in its implanted orientation than would be provided if the curvature of the bearing surfaces between the side walls was the same as or greater than the curvature of the projections. In addition, the curvature of the bearing surfaces between the sidewalls reduces point loading of the interbody spacer at the edges where the upper and lower bearing surfaces join with the respective adjacent side walls, this reducing subsidence. The ends of the projections can be chamfered where they connect to the side walls to further facilitate rotation of the spacer in situ.

These and other aspects and advantages of the present invention will become apparent to those skilled in the art from the description of the illustrated embodiments set forth below.

BRIEF DESCRIPTION OF THE DRAWINGS

FIG. 4A is a plan view of an implant holding member of the inserter.

FIG. 4B is a section view along line 4B-4B of FIG. 4A.

FIG. 4C is a left end elevation view of the holding member shown in FIG. 4B.

FIG. 4D is a plan view of the holding member shown in FIG. 4B.

DESCRIPTION OF THE ILLUSTRATED EMBODIMENTS

Figure 1:
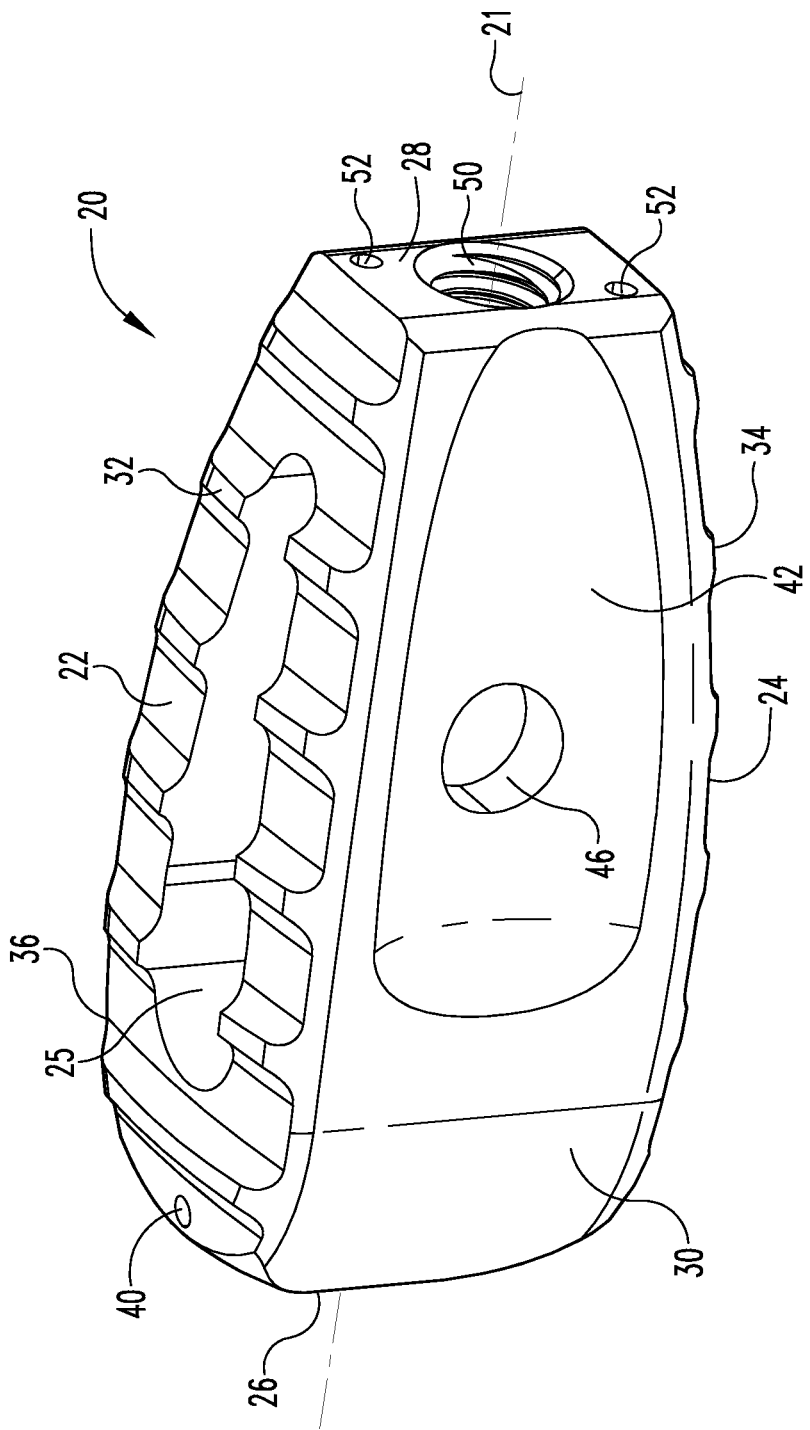
FIG. 1 is a perspective view of an interbody spacer.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

Figure 2A:
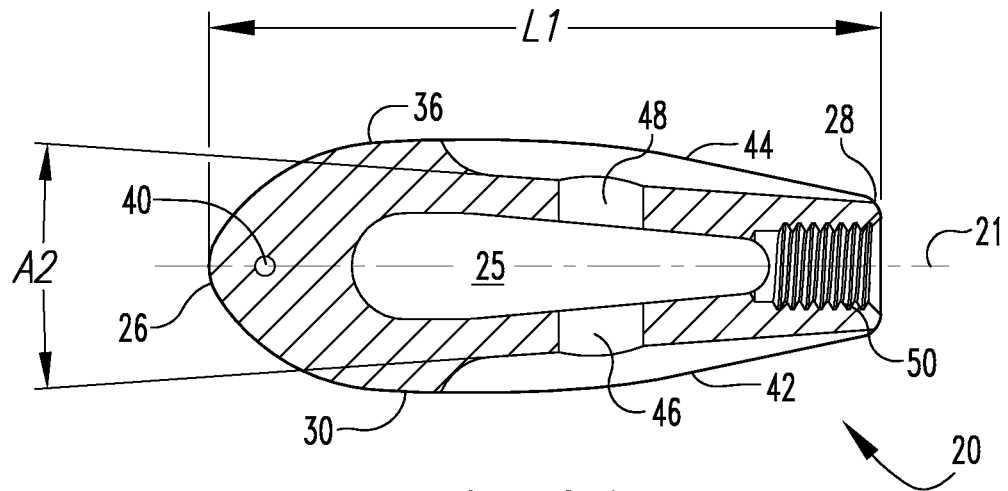
FIG. 2A is a section view of the interbody spacer of FIG. 1 along line 2A-2A of FIG. 2B.
Figure 2C:
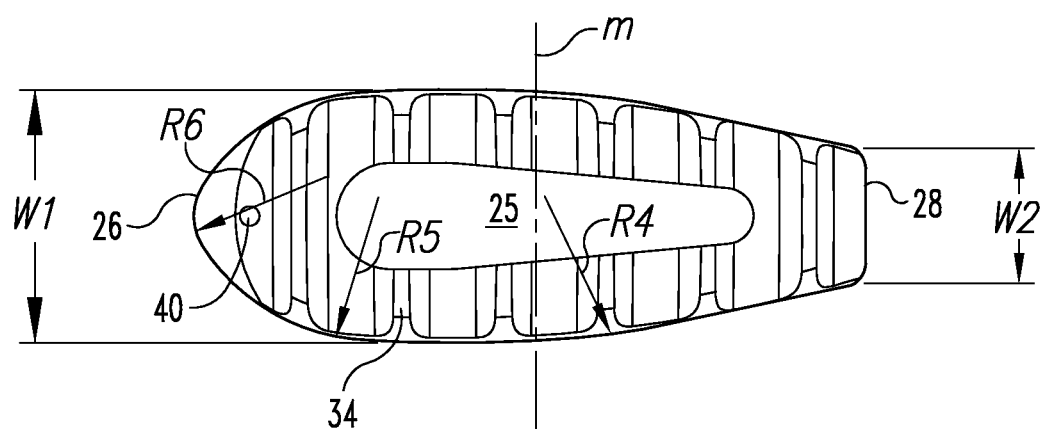
FIG. 2C is a plan view of the interbody spacer of FIG. 2A looking from line 2C-2C of FIG. 2B.
Figure 2E:
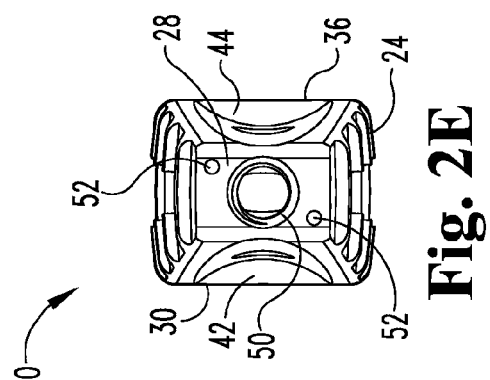
FIG. 2E is a right end side elevation view of the interbody spacer of FIG. 2B looking toward the trailing end of the interbody spacer.
Figure 2B:
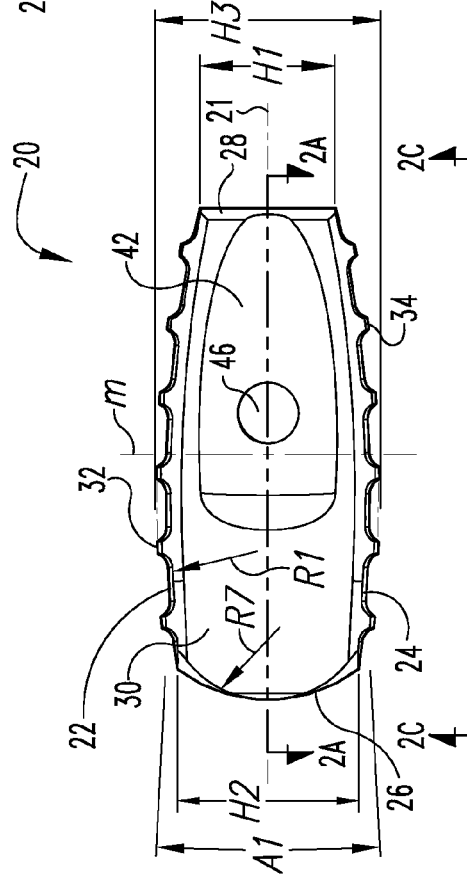
FIG. 2B is a side elevation view of the interbody spacer of FIG. 2A.

Referring now to FIG. 1, there is shown an interbody spacer 20 with a height in the sagittal plane, a length in the axial plane, and a width in the coronal plane configured for placement between two adjacent vertebral bodies. Spacer 20 includes an elongated body extending along and centered on a longitudinal axis 21. The body of spacer 20 includes an upper bearing surface 22 and an oppositely facing lower bearing surface 24 spaced from one another by a first lateral side wall 30 and an oppositely facing second lateral side wall 36. Upper bearing surface 22 and lower bearing surface 24 terminate at a trailing end 28 and at an opposite leading end portion 26. Upper bearing surface 22 includes a series of projections 32 and lower bearing surface 24 includes a similar series of projections 34. Projections 32 and projections 34 are spaced longitudinally from the adjacent projection and each projection extends across the width of the body between side walls 30, 36 orthogonally to longitudinal axis 21. Each of the lateral side walls 30, 36 includes a slot 42, 44, respectively, extending therein. Slots 42, 44 are concavely curved into the respective side wall 30, 36 in a direction between bearing surfaces 22, 24, and also extend linearly and longitudinally from trailing end 28 to an end of the respective slot that is offset toward leading end portion 26 from mid-length plane M (FIG. 2B.) Each of the slots 42, 44 includes a hole 46, 48 therein that communicates with cavity 25. In other embodiments, slots 42, 44 do not include any holes 46, 48 and are isolated from cavity 25. Trailing end 28 also includes a receptacle 50 extending on longitudinal axis 21 to cavity 25.

In one embodiment, the body of spacer 20 is formed of a radiolucent material and includes a series of radiopaque markers embedded therein to accommodate visualization of spacer 20 during and after insertion into an intervertebral disc space when the implant is formed of substantially radiolucent material. Radiopaque markers 40 are positioned at the leading end 26 of spacer 20 at the transition point between leading end portion 26 and upper bearing surface 22 and lower bearing surface 24, respectively. Radiopaque markers 52 are positioned in opposite corners of trailing end 28, respectively, adjacent respective ones of upper and lower bearing surfaces 22, 24. In one specific embodiment, radiopaque markers 40 and 52 are pins inserted into the spacer material prior to formation of its exterior geometry. Each of the radiopaque markers 40, 52 has an exterior surface substantially identical to and co-terminus with the geometry of the adjacent exterior surface of spacer 20. Thus, upon implantation, a surgeon may be able to correctly visualize through x-ray imaging or other techniques the exact relationship between the surfaces of spacer 20 and the surrounding bone structures. Various spacer materials are contemplated that may include PEEK, other polymers including resorbable polymers, ceramics, composites, bone or bone substitute materials, and biocompatible metals such as stainless steel, titanium, or tantalum. Materials are listed by way of example, and any suitable biocompatible may form the spacer body described herein. Furthermore, spacer 20 is illustrated as a body with an internal cavity 25 and of substantially uniform material. It will be appreciated that teachings of the present invention may be applied to interbody spacers having solid bodies or pores for receiving bone growth promoting material. Still further, the body of the spacer may be formed with layers of uniform or non-uniform materials, such as bone and other composite materials, to form a spacer body as described herein.

Referring now to FIGS. 2A through 2E, there are shown various views of interbody spacer 20. Upper bearing surface 22 has a convex shape with a radius of curvature R1 extending from leading end portion 26 to trailing end 28. In a similar manner, lower bearing surface 24 has a convex shape with a radius of curvature from leading end portion 26 to trailing end 28 substantially identical to R1. The height of the body of spacer 20 at leading end portion 26 is H2. The height of the body of spacer 20 at trailing end 28 is H1. As illustrated in FIG. 2B, H2 is substantially greater than H1. Furthermore, the body of spacer 20 forms a maximum height H3 at a location defined by the crests of at least one of the set of projections 30, 32, which are offset toward trailing end 28 from the junction of leading portion 26 and bearing surfaces 22, 24. The relationship between H1 and H2 is created by the location of the center point for the radius of curvature R1 for upper bearing surface 22 and the corresponding location of the center point for the radius of curvature forming lower bearing surface 24. More specifically, the center point for R1 is offset from mid-length plane M towards the leading end portion 26. As used herein, "mid-length" means located one half the distance between the terminus ends of the leading end portion 26 and the trailing end 28 on longitudinal axis 21. Thus, the center point for R1 is longitudinally offset from mid-length plane M toward leading end portion 26 of the spacer 20. The differing heights H1, H2 establish a lordosis angle A1 between upper and lower bearing surfaces 22, 24 to establish a desired angulation between endplates of the adjacent vertebrae. In other embodiments, heights H1, H2 are the same when lordosis is not required, and the maximum height between bearing surfaces 22, 24 is located at near or adjacent mid-length plane M. In one specific embodiment, the non-lordotic maximum height location is located within 5 millimeters of the midpoint plane.

Figure 2D:
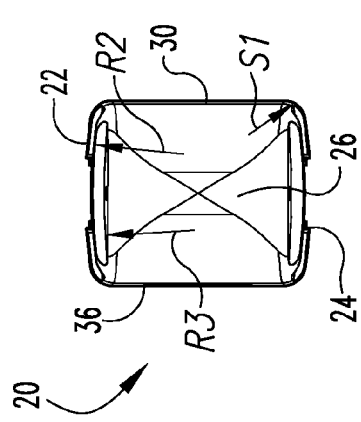
FIG. 2D is a left end elevation view of the interbody spacer of FIG. 2B looking toward the leading end portion of the interbody spacer.

Spacer 20 has a length L1 from leading end portion 26 to trailing end 28. Length L1 is sized to extend substantially across a vertebral endplate of the vertebrae to be supported. For example, length L1 can vary from 18 millimeters to 32 millimeters, although other lengths are not precluded. The convexly curved upper and lower bearing surfaces 22, 24 fit with the concavity of the vertebral endplates to provide an intimate fit therewith. Each of the upper bearing surface 22 and the lower bearing surface 24 include a series of projections 32 and 34, respectively. Each projection includes a truncated crest defined by a curved surface that is connected with the respective bearing surface 22, 24 with concavely rounded transitions that blend into the respective portion of the bearing surface 22, 24 extending between adjacent projections. As shown in FIGS. 2D and 2E, the truncated ends of projections 32, 34 lie on an arc defined by a radius R2 with the arc extending orthogonally to longitudinal axis 21 between side walls 30, 36. Bearing surfaces 22, 24 lie on an arc defined by a radius R3 with the arc extending orthogonally to longitudinal axis 21 between side walls 30, 36. Radius R2 is substantially less than radius R3 so that the projections are more pronounced at the center of spacer 20 to provide better engagement and bite or penetrate into the vertebrae to resist counter-rotation after spacer 20 is rotated to its implantation orientation. In addition, point loading at or near the junction of the bearing surface and its respective projections with the adjacent side wall is reduced. Furthermore, the reduced height of the projections 32, 34 at the junction with the adjacent side wall minimizes disruption to the endplates during rotation of spacer 20. The larger radius R3 provides bearing surfaces in the transverse direction with increased stability for spacer 20 in the disc space when its final rotated implantation orientation has been obtained. In one specific embodiment, radius R2 is about 35-40% less than radius R3. Furthermore, each of the ends of each projection 32, 34 that transition to the respective side wall 30, 36 is rounded from its respective crest to the adjacent side wall to provide a smooth transition to eliminate an abrupt surface change at the corners of the spacer body that may have a tendency to engage or tear tissue during rotation of spacer 20 about longitudinal axis 21.

Figure 2F:
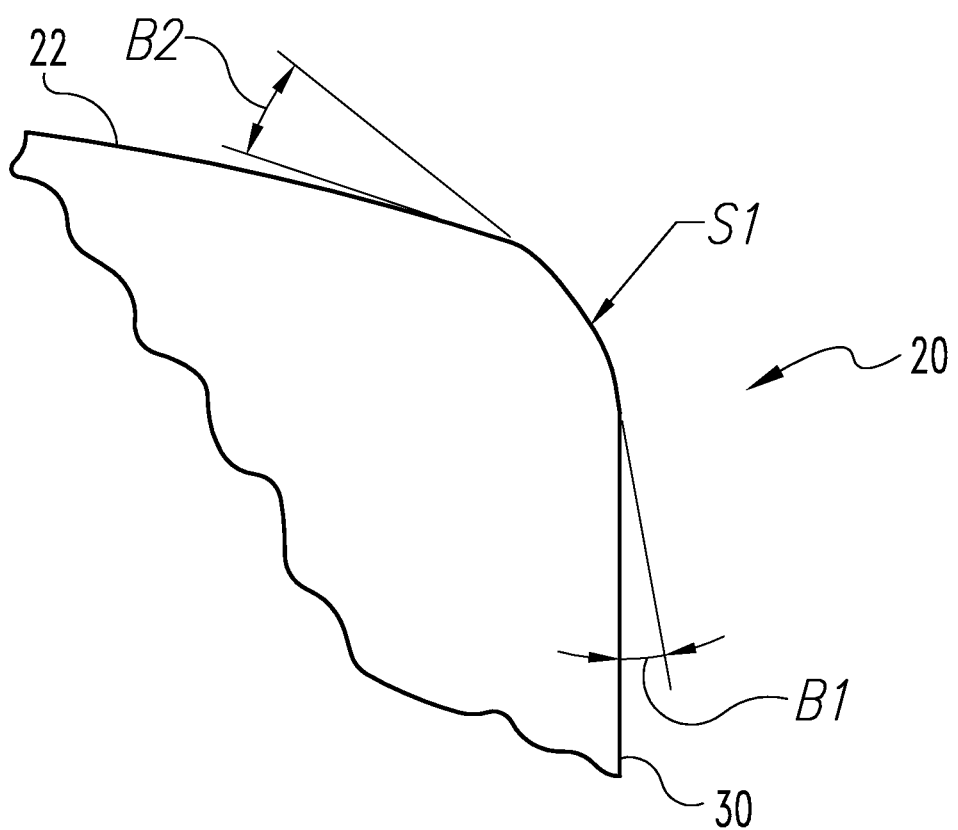
FIG. 2F illustrates one embodiment of a corner configuration for the interbody spacer.

Each of the corners or edges of spacer body 20 that connect the adjacent side wall 30, 36 with the adjacent upper or lower bearing surface 22, 24 are defined by an arcuate surface, such as arcuate surface S1 in FIG. 2D. Surface S1 can include a simple curvature that lies on a single arc defined by a radius. However, it is also contemplated that surface S1 can be defined by multiple continuous arcs having varying radii to facilitate rotation of the corner or edge along the vertebral endplate. In another embodiment shown, shown in FIG. 2F, surface S1 can intersect the adjacent outer surface of side wall 30, 36 so that a tangent of surface S1 at the intersection of surface S1 and the lateral side wall lies on or forms a small angle, such as angle B1, with the outer surface of the side wall. In contrast, the tangent of surface S1 at the intersection of surface S1 with the respective adjacent upper or lower bearing surface 22, 24 does not lie on or substantially parallel to the respective upper or lower bearing surface 22, 24, but forms an angle B2 that is larger than angle B1. Thus, the tangent of surface S1 at the side wall intersection is substantially closer to lying on the adjacent side wall than the tangent of surface S1 at its bearing surface intersection is to lying on or parallel to the bearing surface.

In FIGS. 2D and 2E, there is shown end views from the trailing end and leading end portion of spacer 20. Lateral side walls 30 and 36 are substantially linear in a direction extending from upper bearing surface 22 to lower bearing surface 24. As shown in FIGS. 2A and 2C, side walls 30, 36 are convexly and laterally outwardly curved from trailing end 28 to leading end 25. A major portion of the length of each side wall 30, 36 lies on an arc defined by a radius R4 and this major length portion extends from trailing end 28 to a location offset from mid-length plane M toward leading end portion 26. The size of radius R4 varies depending on length L1 of spacer 20 and increases as the length L1 increases. For example, one specific embodiment provides a radius R4 of 35 millimeters for spacer with length L1 of 18 millimeter and an R4 of 80 millimeters for a spacer length L1 of 32 millimeters. Side walls 30, 36 are more aggressively curved on an arc defined by a radius R5 from leading end portion 26 to the location to form a junction with the major length portion of side walls 30, 36 lying on the arc defined by radius R4. Side walls 30, 36 define a maximum width W1 at the junction, and a smaller width W2 at trailing end 28. In one specific example, radius R5 is about 7 millimeters and radius R4 is about 5 to 11 times larger than radius R4. Leading end portion 26 forms a bullet shape between side walls 30, 36 that is defined by an arc having a small radius R6 between and connecting side walls 30, 36. In one specific embodiment, radius R6 is about 2 millimeters, maximum width W1 is about 9 millimeters, and width W2 is about 4.5 millimeters. Other embodiments contemplate other values for these dimensions that maintain the general proportions between various portions of spacer 20.

The bullet-shape profile of leading end portion 26 in the direction between side walls 30, 36 facilitates insertion of spacer 20 into a collapsed disc space with spacer 20 oriented so that side walls 30, 36 face respective ones of the vertebral endplates. Furthermore, the transition of the aggressively rounded leading end portion 26 to the more subtly rounded side wall portions defined by radius R5 allows spacer 20 to initially distract and maintain this initial distraction with a sufficient length of weight bearing surface along side walls 30, 36 without cutting into the vertebral endplates. In addition, the length of upper and lower bearings surfaces 22, 24 can be maximized and extended to a location that is only slightly offset from the leading most end nose portion 26, as shown in FIG. 2C. As shown in FIG. 2B, in the direction between bearing surfaces 22, 24, leading end portion 26 includes a terminal end surface that defines a blunt nose that extends on a convex arc defined by a radius R7. Radius R7 varies based on height H1 of spacer 20. In one specific example, when height H1 is 10 millimeters radius R7 is about 7.5 millimeters, and when height H1 is 18 millimeters radius R7 is about 14 millimeters. The large radius of leading end portion 26 between bearing surfaces 22, 24 also maximizes the length of bearing surfaces 20, 22 available to contact the vertebral endplates when spacer 20 is rotated around longitudinal axis 21 from its insertion orientation to its implanted orientation.

FIG. 2A illustrates a section view of spacer 20 that shows slots 42, 44 in side walls 30, 36. Slots 42, 44 diverge from trailing end 28 in a direction toward leading end portion 26 at an angle A2. This provides a wedge fit with the inserter, discussed further below. In addition, as shown in FIG. 2B, the height of slots 42, 44 increases in the direction toward leading end portion 26 so that the upper and lower edges of slots 42, 44 parallel respective ones of upper and lower bearing surfaces 20, 22 along a major portion of the length of slots 42, 44. Trailing end 28 includes a planar surface at the terminal end of spacer 20, and slots 42, 44 extend through the planar wall surface of trailing end 28. Slots 42, 44 may have a length ranging from 4 millimeters to 17 millimeters from trailing end 28. In one specific embodiment, slots 42, 44 extend from trailing end 28 to an opposite end thereof that is located adjacent to midpoint plane M. In addition, receptacle 50 extends between trailing end 28 and cavity 25, although receptacle 50 may also include a blind end. In the illustrated embodiment, receptacle 50 includes an inner thread profile to threadingly engage an inserter. Other embodiments contemplate non-threaded and/or non-circular receptacles, multiple receptacle, or spacers without a receptacle. In still other embodiments, trailing end 28 includes slots, ridges, or other features to enhance engagement with an inserter, either with or without a receptacle 50 and slots 42, 44. Cavity 25 includes an elongated ovular shape extending from leading end portion 26 toward trailing end 28. The width of cavity 25 tapers in a direction toward trailing end 28 to maintain a minimum wall thickness for spacer 20 along cavity 25.

Figure 3:
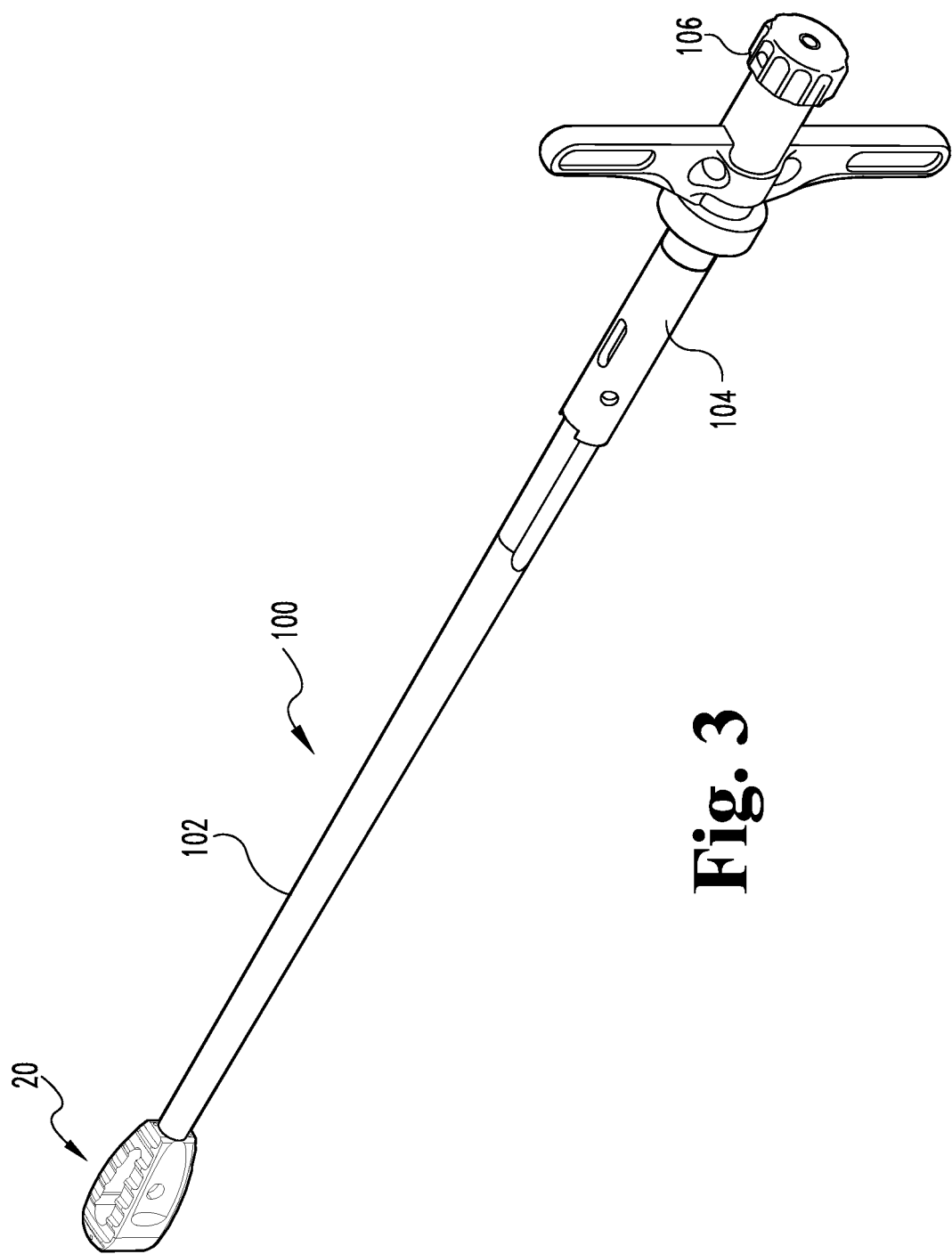
FIG. 3 is a perspective view of the interbody spacer coupled to one embodiment inserter instrument.

Referring now to FIG. 3, spacer 20 is shown connected to one embodiment inserter 100. Inserter 100 includes an elongated holding member 102 and a handle 104 removably or permanently connected to the proximal end of holding member 102. Handle 104 includes a T-shaped grip to facilitate application of rotational forces to holding member 102 to rotate spacer 20 when it is implanted in the disc space. Inserter 100 also includes a locking member 106 extending through handle 104 and holding member 102 to engage receptacle 50 of spacer 20. As further shown in FIGS. 4A-4D, holding member 102 includes a distal end structure with a pair of fingers 108, 110 that are received in slots 42, 44 of spacer 20. Holding member 102 also defines a longitudinal passage 112 that receives locking member 106 so that a threaded distal end portion of locking member 106 projects between fingers 108, 110 to engage receptacle 50 of spacer 20. The holding structure also includes a pair of upper and lower flanges 114, 116 that extend along upper and lower bearing surfaces 22, 24, or in recesses in upper and lower bearing surfaces 22, 24, to further enhance the grip of inserter 100 with spacer 20 as it is rotated in the disc space.

Figure 5:
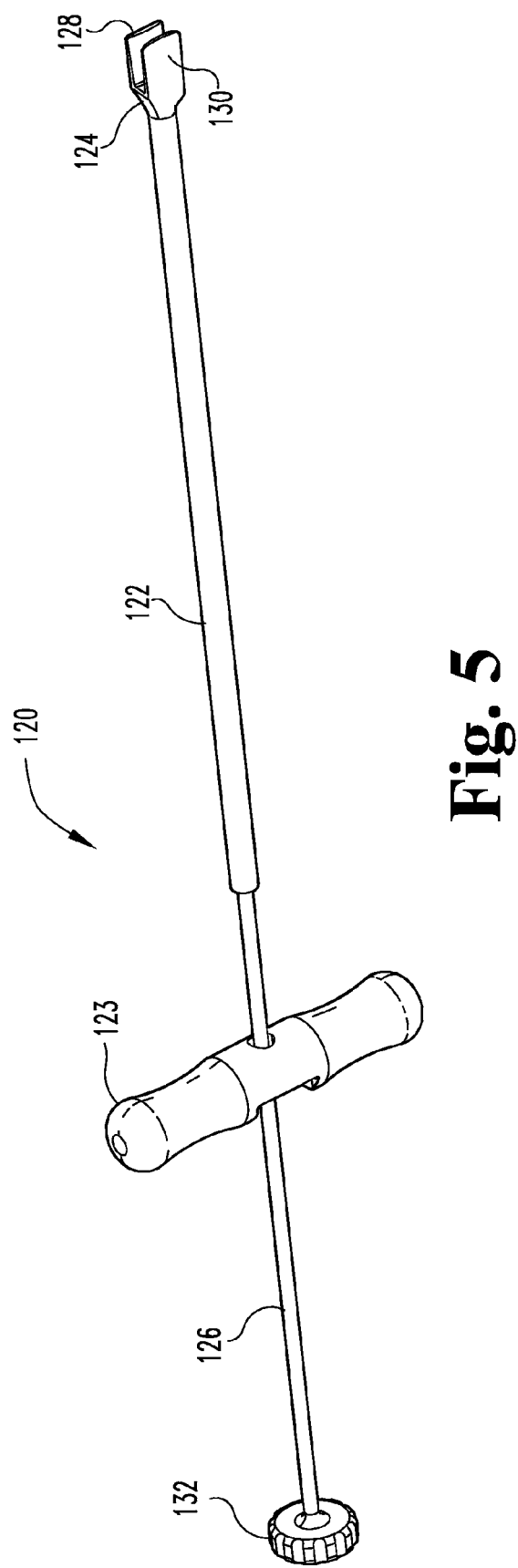
FIG. 5 is a partially exploded perspective view of another embodiment inserter instrument.
Figure 6:
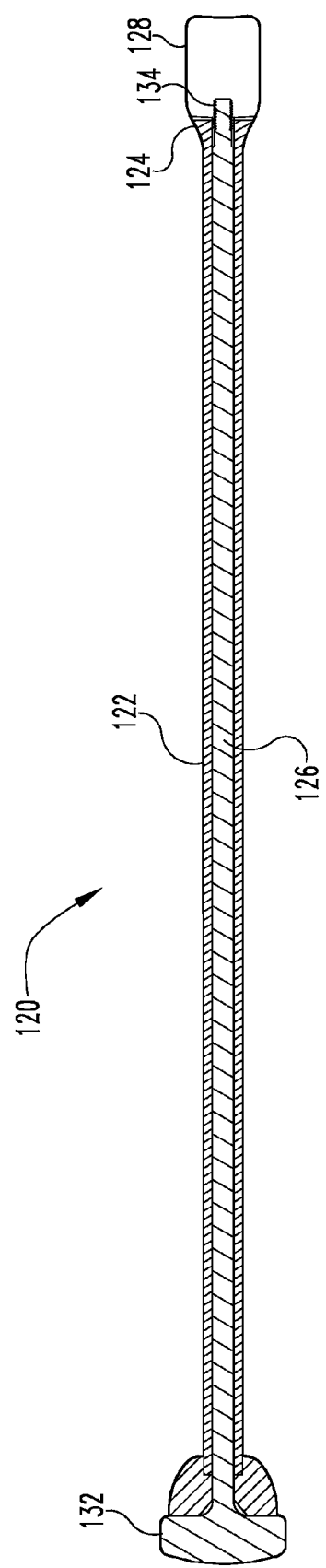
FIG. 6 is a longitudinal section view of the inserter instrument of FIG. 5.

Referring now to FIGS. 5-6, there is shown another embodiment inserter 120 for engaging spacer 20. Inserter 120 includes an inner locking member 126 slidably disposed within an outer tube 122. Outer tube 122 includes a distal holding structure 124 that includes a pair of opposing fingers 128, 130 spaced apart by gap that receives spacer 20 therebetween. Outer tube 122 also includes a handle 123 that is shown in exploded view from outer tube 122 but normally is rigidly attached to outer tube 122. It will be appreciated that thumb wheel 132 may be rotated with respect to outer tube 122 to engage end member 134 of locking member 126 in receptacle 50 and draw spacer 20 between fingers 128, 130 with fingers 128, 130 received in slots 42, 44. Fingers 128, 130 include convexly curved facing surfaces that match the concave profile of slots 42, 44 and diverge to provide an intimate fit therewith. As a result, rotational force applied to the spacer by inserter 120 is distributed along a major portion of the length and height of spacer 20. Further, the mating of the concave and convex surfaces of the spacer and inserter inhibits the concentration of force at a particular location on the spacer during rotation. As a result, less implant material is needed, or a weaker material such as bone may be employed, to counteract the rotational forces that may be experienced during rotation of the spacer within the disc space.

The above described spacer includes a variety of improved features. While all of these features have been disclosed with reference to the described embodiment, it will be appreciated that one or any combination of features may be utilized with an improved interbody spacer. Further, while specific dimensions were disclosed suitable for spinal anatomy in the lumbar spine of some patients, a spacer may be configured with other dimensions suitable for interbody spacers at various levels, lumbar, thoracic, and cervical, of the spine for a variety of patient populations. For example, in an average patient population the anterior height of the device may range from 4 millimeters to 18 millimeters. Similarly, the posterior height of the device may range from 2 millimeters to 16 millimeters. Within this range, the longitudinal offset of the center point defining the arc of the upper and lower bearing surfaces may be adjusted to create lordotic angulations ranging from 0 to 30 degrees.

Figure 8:
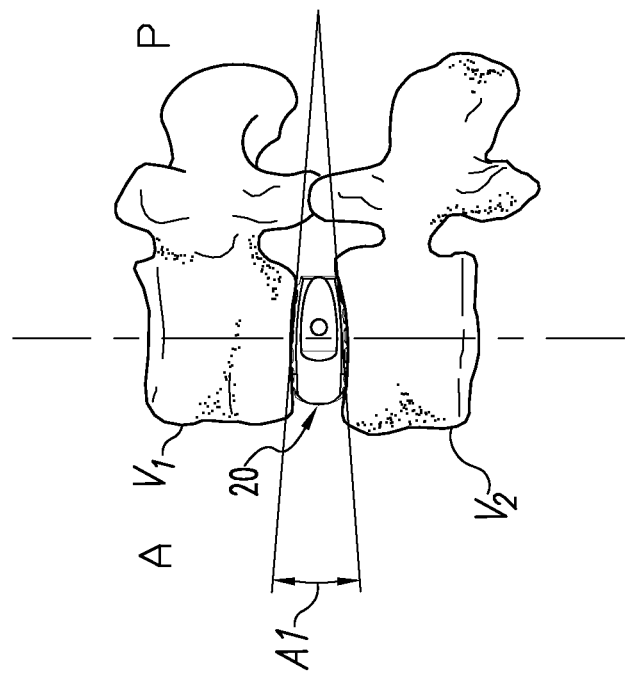
FIG. 8 is a side elevation view of the spinal column segment showing the interbody spacer rotated to an implantation orientation while positioned in the disc space.
Figure 7:
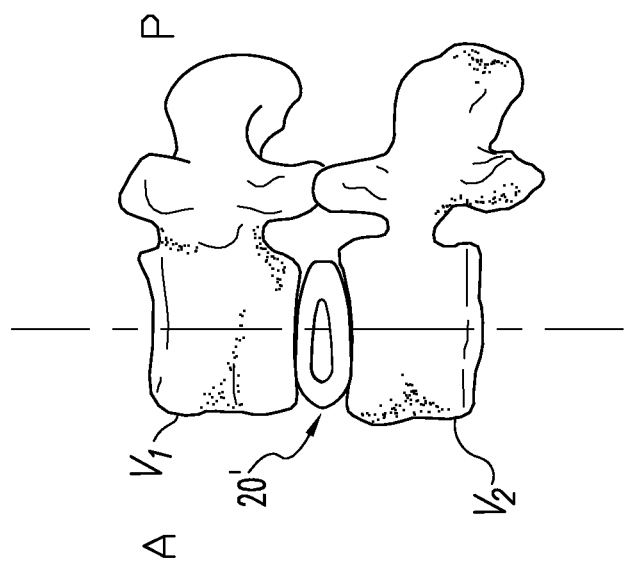
FIG. 7 is a side elevation view of a spinal column segment showing the interbody spacer in an insertion orientation while positioned in the disc space.

FIGS. 7-8 illustrate a spacer 20 implanted in a disc space between two adjacent vertebrae V1 and V2. Spacer 20 may be inserted into the disc space from a posterior approach P with the bone engaging surfaces positioned laterally, as shown by the orientation of spacer 20' in FIG. 7, and rotated into the spacing position after insertion into the disc space, as shown by spacer 20 in FIG. 8. Alternatively, spacer 20 may be impacted directly into the disc space with the upper and lower bearing surfaces positioned for immediate engagement with the endplates of vertebrae V1 and V2. In addition, spacer 20 may be inserted into the disc space from an anterior approach A, a lateral approach, or an oblique approach. In any approach, spacer 20 may be inserted directly by impaction without rotation, or oriented with the bone engaging surfaces facing laterally and then rotated after the spacer 20 is positioned in the disc space. It will be appreciated that the smooth, rounded features of the spacers described herein may limit the potential of the spacer to snag or abrade soft tissue, including neurological structures, during the insertion and/or rotation procedure. Still further, the bullet nose shape of the leading end of the spacer allows insertion in a collapsed disc space with the spacer in orientation of spacer 20' and prevents damage to the anterior annulus in the event that the spacer is advanced too far anteriorly during implantation. The convexly rounded lateral side walls recapitulate the adjacent vertebrae during insertion.

Figure 9:
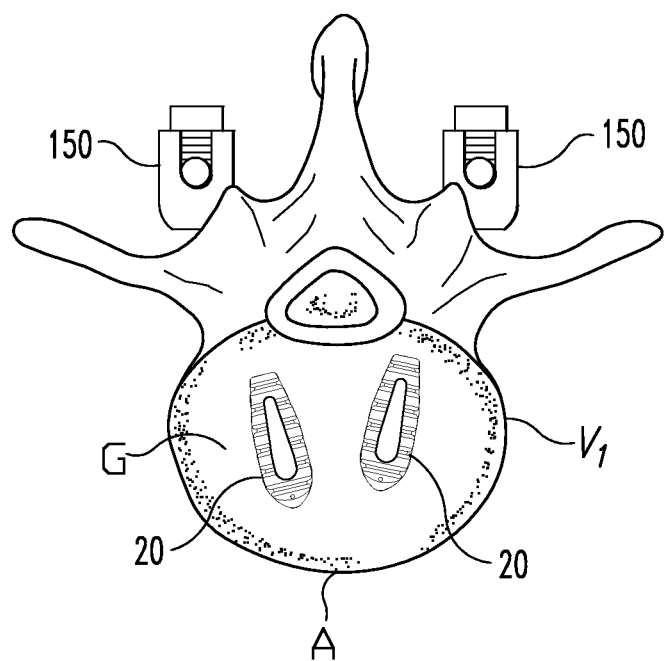
FIG. 9 is a plan view of a vertebral body showing a pair of interbody spacers positioned in the disc space and external fixation devices.
Figure 10:
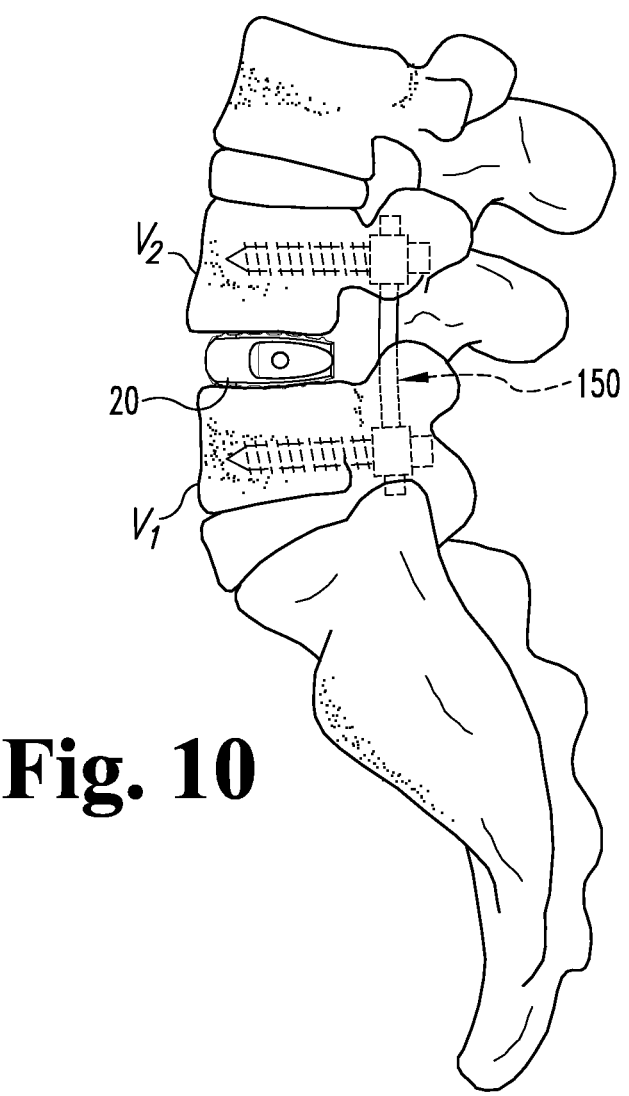
FIG. 10 is a side elevation view of the spinal column segment showing an interbody spacer in the disc space in its implanted orientation and external fixation devices engaged to the vertebrae.

As shown in FIG. 9, graft material G may be positioned around the lateral aspects of each spacer 20 to completely or partially fill the disc space with graft material between and outside the spacers 20. Cavity 25 may alternatively or additionally be filled with graft material G. Fixation devices 150 in the form of bone anchors and connecting rods may be provided outside the disc space to provide further stabilization if desired such as shown in FIG. 10. If slight adjustments to the angle of lordosis between vertebrae V1 and V2 are desired, a distraction or compression tool may be applied to devices 150 to move the vertebrae across the convex upper or lower surface of the fixation devices 150 to modify the angulation between V1 and V2.

Figure 11:
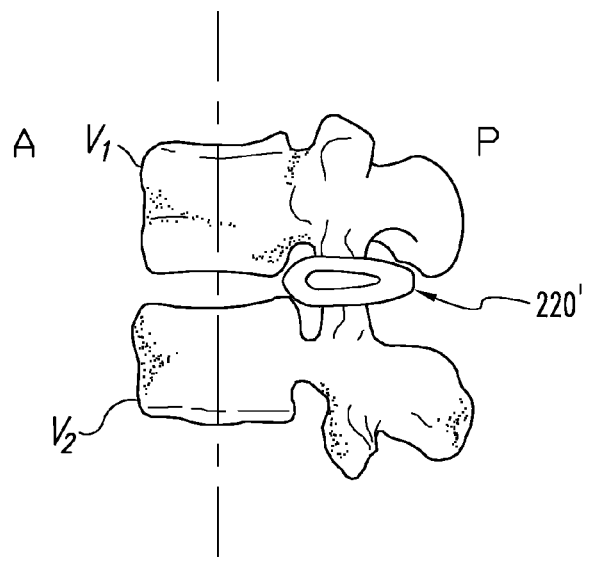
FIG. 11 is a side elevation view of a spinal column segment showing another embodiment interbody spacer being inserted to initially distract the adjacent vertebrae.
Figure 12:
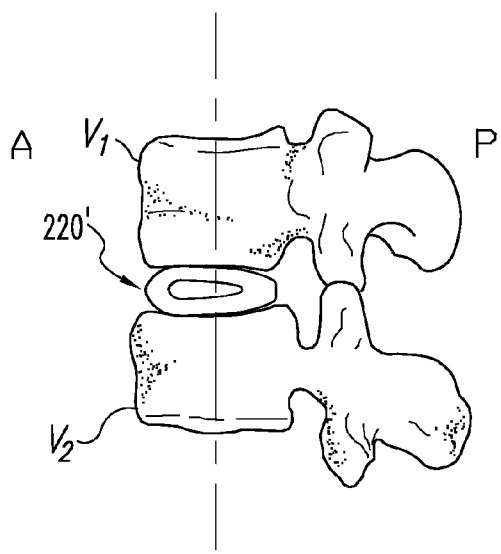
FIG. 12 is a side elevation view of a spinal column segment showing the interbody spacer in an insertion orientation while positioned in the disc space.
Figure 13:
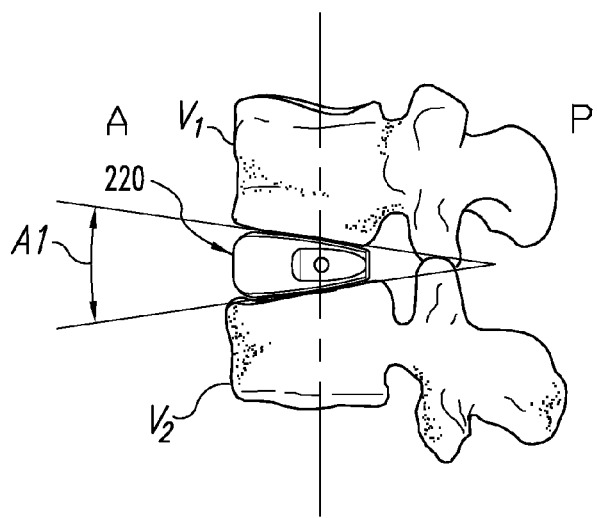
FIG. 13 is a side elevation view of the spinal column segment showing the interbody spacer rotated to an implantation orientation while positioned in the disc space.

FIGS. 11-13 illustrate another embodiment spacer 220 for implantation in a disc space. Spacer 220 can be the same or similar to spacer 20 discussed above, but includes an aggressively tapered height so that the leading end portion is substantially greater in height the trailing end portion to establish lordosis in rotated to its final position. In one embodiment, spacer 220 includes smooth upper and lower bearing surfaces that lack projections. In another embodiment, spacer 220 includes projections like spacer 20 discussed above. In FIG. 11, spacer 220' is shown rotated to an insertion orientation with its leading end portion positioned at an entrance between the endplates for insertion into the spinal disc space to initially distract vertebrae V1 and V2 from a posterior approach P. Insertion of spacer 220' (and also spacer 20') into a collapsed disc space D as shown in FIG. 12 is facilitated by the configuration the lateral side walls of the spacer that face the endplates of the vertebrae V1, V2 when in its insertion orientation. Spacer 220' is advanced into the disc space to provide an initial distraction of vertebrae V1, V2. In FIG. 13, spacer 220 is rotated a quarter turn about its axis so that the upper and lower bearing surfaces of spacer 220 contact the endplates of the adjacent vertebrae V1, V2. Rotation of spacer 22 creates lordosis angle A1 between the endplates when spacer 22 is in its final implanted orientation.

Figure 14:
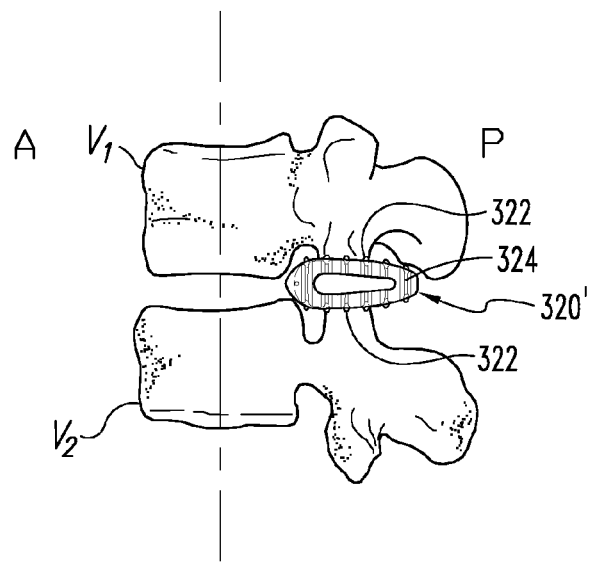
FIG. 14 is a side elevation view of a spinal column segment showing another embodiment interbody spacer being inserted to initially distract the adjacent vertebrae.
Figure 15:
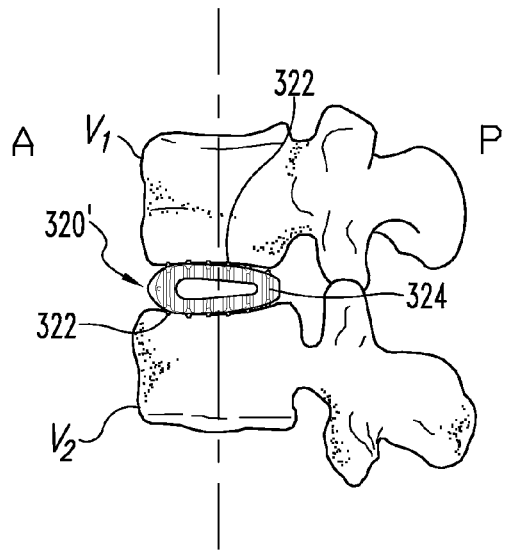
FIG. 15 is a side elevation view of a spinal column segment showing the interbody spacer in an insertion orientation while positioned in the disc space.
Figure 16:
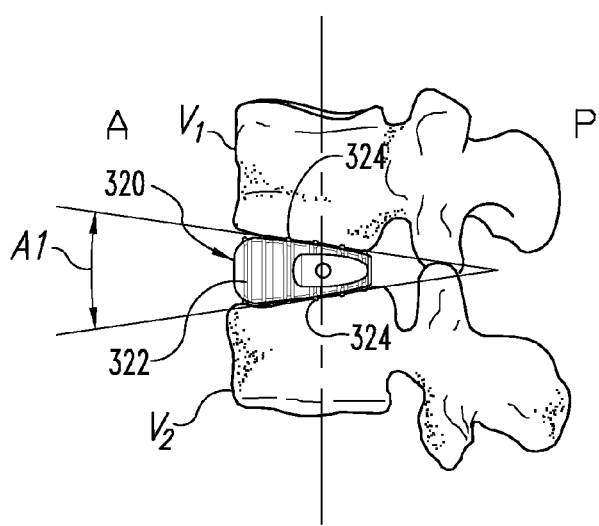
FIG. 16 is a side elevation view of the spinal column segment showing the interbody spacer rotated to an implantation orientation while positioned in the disc space.

FIGS. 14-16 illustrate another embodiment spacer 320 for implantation in a disc space. Spacer 320 can be the same or similar to spacer 20 or 220 discussed above, but includes projections on its lateral side walls so that the surgeon can select to leave the spacer implanted in its initial insertion orientation if a desired fit is achieved, or later rotate the spacer if a better fit is desired. In FIG. 14, spacer 320' is shown rotated to an insertion orientation with its leading end portion positioned at an entrance between the endplates for insertion into the spinal disc space to initially distract vertebrae V1 and V2 from a posterior approach P. Spacer 320' is advanced into the disc space to provide an initial distraction of vertebrae V1, V2 as shown in FIG. 15. If the desired fit is achieved, then projections 322 on its side walls engage the vertebral endplates and provide stability for the implanted spacer 320' in this initial insertion orientation. If a better fit is desired, spacer 320 is rotated a quarter turn about its axis so that the upper and lower bearing surfaces of spacer 320 and their projections 324 contact the endplates of the adjacent vertebrae V1, V2 in its final implanted orientation.

Although various embodiments have been described as having particular features and/or combinations of components, other embodiments are possible having a combination of any features and/or components from any of embodiments as discussed above. As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof. Furthermore, the terms "proximal" and "distal" refer to the direction closer to and away from, respectively, an operator (e.g., surgeon, physician, nurse, technician, etc.) who would insert the medical implant and/or instruments into the patient. For example, the portion of a medical instrument first inserted inside the patient's body would be the distal portion, while the opposite portion of the medical device (e.g., the portion of the medical device closest to the operator) would be the proximal portion.

While the invention has been illustrated and described in detail in the drawings and foregoing description, the same is to be considered as illustrative and not restrictive in character, it being understood that all changes and modifications that come within the spirit of the invention are desired to be protected.

What is claimed is:

1. An interbody spacer for positioning between vertebrae, comprising:
    an elongated central body portion extending along a longitudinal axis between a leading end portion and a trailing end opposite said leading end portion, said body portion including a pair of opposite lateral side walls extending transverse to said longitudinal axis from said leading end portion to said trailing end to define a length of said body portion, said body portion defining a mid-length plane that is orthogonal to said longitudinal axis, said body portion comprising a receptacle extending along said longitudinal axis through said trailing end, said receptacle comprising a blind end;
    an upper bearing surface extending along said longitudinal axis that is curved between said leading end portion and said trailing end, said upper bearing surface for placement against an endplate of a superior vertebra;
    an opposite lower bearing surface extending along said longitudinal axis that is curved between said leading end portion and said trailing end, said lower bearing surface for placement against an endplate of an inferior vertebra, said opposite upper and lower bearing surfaces defining a maximum height between said bearing surfaces at a first location that is offset from said mid-length plane toward said leading end portion, wherein:
    said lateral side walls each define a continuous convexly curved profile extending from said leading end portion to said trailing end, said continuous convexly curved profiles defining a maximum width of said body portion between said lateral side walls at a second location that is offset from said mid-length plane toward said leading end portion; and said upper and lower bearing surfaces each including a series of projections extending outwardly therefrom, said projections having a uniform cross sectional shape, said projections being spaced longitudinally from one another from said leading end portion to said trailing end, one of said projections adjacent said leading end portion and one of said projections adjacent said trailing end extending continuously from one of said lateral side walls to the other of said lateral side walls.

2. The interbody spacer of claim 1, wherein said lateral side walls each include an elongated slot therein that extends from said trailing end to an opposite end of said slot that is located adjacent said mid-length plane.

3. The interbody spacer of claim 2, wherein said elongated slots each include a height that increases from said trailing end toward said opposite end.

4. The interbody spacer of claim 3, wherein said elongated slots diverge away from one another in a direction extending from said trailing end toward said leading end portion.

5. The interbody spacer of claim 1, wherein said central body portion defines a cavity that extends between and opens at each of said upper and lower bearing surfaces.

6. The interbody spacer of claim 5, wherein:
said lateral side walls each include an elongated slot therein that extends from said trailing end to an opposite end of said slot that is located adjacent said mid-length plane; and
said elongated slots are spaced apart from said cavity.

7. The interbody spacer of claim 1, wherein said projections each extend transverse to said longitudinal axis.

8. The interbody spacer of claim 1, wherein said projections each have a truncated crest extending between said lateral side walls and said truncated crests each are defined by a first arc having a first radius and said upper and lower bearing surfaces each extend between said lateral side walls and each are defined by a second arc having a second radius, wherein said second radius is greater than said first radius.

9. The interbody spacer of claim 8, wherein opposite ends of each projection are rounded from an adjacent one of said lateral side walls to said crest of said projection to facilitate rotation of said body portion about said longitudinal axis.

10. The interbody spacer of claim 8, wherein:
said truncated crests of said projections on at least one of said upper and lower bearing surfaces further lie on a third arc having a third radius with said third arc extending from said leading end portion to said trailing end;
at least one of said upper and lower bearing surfaces further lies on a fourth arc having a fourth radius with said fourth arc extending from said leading end portion to said trailing end; and
said truncated crests define a maximum height of said body portion at a location that is offset toward said trailing end from a junction of said upper and lower bearing surfaces and said leading end portion.

11. The interbody spacer of claim 1, wherein said continuous convexly curved profile of each of said lateral side walls are defined by a first arc having a first radius with said first arc extending from said trailing end to said second location, and said continuous convexly curved profile of each of said lateral side walls are defined by a second arc having a second radius with said second arc extending from said second location to said leading end portion, said first radius being greater than said second radius so that said lateral side walls converge toward said leading end portion.

12. The interbody spacer of claim 11, wherein said first radius is in the range of 5 to 11 times larger than said second radius, and said lateral side walls are connected to one another by a nose at said leading end portion that is defined by a third arc having a third radius, wherein said second radius is greater than said third radius.

13. The interbody spacer of claim 12, wherein said nose connects said upper and lower bearing surfaces to one another with an end surface that is defined by a fourth arc having a fourth radius, wherein said fourth radius greater than said third radius.

14. The interbody spacer of claim 1, wherein:
said central body portion defines a cavity that extends between and opens at each of said upper and lower bearing surfaces; and
said receptacle is spaced apart from said cavity by said blind end.

15. An interbody spacer for positioning between vertebrae, comprising:
an elongated central body portion extending along a longitudinal axis between a leading end portion and a trailing end opposite said leading end portion, said body portion including a pair of opposite lateral side walls extending transverse to said longitudinal axis from said leading end portion to said trailing end to define a length of said body portion, said body portion defining a mid-length plane that is orthogonal to said longitudinal axis, said body portion comprising a receptacle extending along said longitudinal axis through said trailing end, said receptacle comprising a blind end;
an upper bearing surface extending along said longitudinal axis and having a convex curvature between said leading end portion and said trailing end, said upper bearing surface for placement against an endplate of a superior vertebra;
an opposite lower bearing surface extending along said longitudinal axis and having a convex curvature between said leading end portion and said trailing end, said lower bearing surface for placement against an endplate of an inferior vertebra, said opposite upper and lower bearing surfaces defining a maximum height between said upper and lower bearing surfaces at a first location that is offset from said mid-length plane toward said leading end portion, wherein:
said lateral side walls each define a continuous convexly curved profile extending from said leading end portion to said trailing end;
said upper bearing surface and said lower bearing surface each include a series of projections extending outwardly therefrom, said projections having a uniform cross sectional shape, the projections each extending transverse to said longitudinal axis and are spaced apart from one another from said leading end portion to said trailing end, one of said projections adjacent said leading end portion and one of said projections adjacent said trailing end extending continuously from one of said lateral side walls to the other of said lateral side walls; and
said projections each have a truncated crest extending between said lateral side walls that are defined by a first arc having a first radius and said upper and lower bearing surfaces each extend between said lateral side walls and are defined by a second arc having a second radius, wherein said second radius is greater than said first radius.

16. The interbody spacer of claim 15, wherein opposite ends of each projection are rounded from an adjacent one of said lateral side walls to said truncated crest of said projection to facilitate rotation of said body portion around said longitudinal axis.

17. The interbody spacer of claim 15, wherein a corner connects each of said lateral side walls to a respective one of said upper and lower bearing surface and each of said corners is defined by an arcuate surface.

18. The interbody spacer of claim 17, wherein a tangent of at least one of said arcuate surfaces at an intersection of said arcuate surface with said lateral side wall is closer to lying on said lateral side wall than a tangent of said arcuate surface at an intersection with said respective one of said upper and lower bearing surfaces is to lying on said respective bearing surface.

19. The interbody spacer of claim 17, where said arcuate surface includes at least one arc defined by a radius.

20. The interbody spacer of claim 15, wherein:
said truncated crests of said projections on at least one of said upper and lower bearing surfaces further lie on a third arc having by a third radius with said third arc extending from said leading end portion to said trailing end;
at least one of said upper and lower bearing surfaces further lies on a fourth arc having a fourth radius with said fourth arc extending from said leading end portion to said trailing end; and
said truncated crests define a maximum height of said body portion at a location that is offset toward said trailing end from a junction of said upper and lower bearing surfaces and said leading end portion.

21. The interbody spacer of claim 15, wherein said lateral side walls include projections extending outwardly therefrom.

22. An interbody spacer for positioning between vertebrae, comprising:
an elongated central body portion extending along a longitudinal axis between a leading end portion and a trailing end opposite said leading end portion, said body portion including a pair of opposite lateral side walls extending transverse to said longitudinal axis from said leading end portion to said trailing end to define a length of said body portion, said body portion defining a mid-length plane that is orthogonal to said longitudinal axis, said body portion comprising a receptacle extending along said longitudinal axis through said trailing end, said receptacle comprising a blind end;
an upper bearing surface extending along said longitudinal axis and having a convex curvature between said leading end portion and said trailing end, said upper bearing surface for placement against an endplate of a superior vertebra;
an opposite lower bearing surface extending along said longitudinal and having a convex curvature between said leading end portion and said trailing end, said lower bearing surface for placement against an endplate of an inferior vertebra, said opposite upper and lower bearing surfaces defining a maximum height between said bearing surfaces at a first location that is located between said trailing end and said leading end portion, wherein:
said upper and lower bearing surfaces each including a series of projections extending outwardly therefrom, said projections having a uniform cross sectional shape, said projections being spaced longitudinally from one another from said leading end portion to said trailing end, one of said projections adjacent said leading end portion and one of said projections adjacent said trailing end extending continuously from one of said lateral side walls to the other of said lateral side walls;
said lateral side walls each define a continuous convexly curved profile extending from said leading end portion to said trailing end, said continuous convexly curved profiles defining a maximum width of said body portion at a second location that is offset from said mid-length plane toward said leading end portion; and
said continuous convexly curved profile of each of said lateral side walls is defined by a first arc having a first radius with said first arc extending from said trailing end to said second location, and said continuous convexly curved profile of each of said lateral side walls is further defined by a second arc having a second radius with said second arc extending from said second location to said leading end portion, said first radius being greater than said second radius so that said lateral side walls diverge from said trailing end to said second location and converge from said second location toward said leading end portion.

23. The interbody spacer of claim 22, wherein:
said first radius is in the range from 5 to 11 times larger than said second radius, and said lateral side walls are connected to one another with a nose at said leading end portion that is defined by a third arc having a third radius, wherein said second radius is greater than said third radius;
said nose connects said upper and lower bearing surfaces to one another with an end surface that is defined by a fourth arc having a fourth radius, wherein said fourth radius is greater than said third radius; and
said central body portion defines a cavity that extends between and opens at each of said upper and lower bearing surfaces.

24. The interbody spacer of claim 22, wherein at least one of said lateral side walls includes projections.

* * * * *

UNITED STATES PATENT AND TRADEMARK OFFICE
CERTIFICATE OF CORRECTION

PATENT NO.           : 9,095,445 B2                                   Page 1 of 1
APPLICATION NO.      : 13/182942
DATED                : August 4, 2015
INVENTOR(S)          : Yu et al.

It is certified that error appears in the above-identified patent and that said Letters Patent is hereby corrected as shown below:

On the title page, item 75, under "Inventors", in Column 1, Line 6, delete "Peter McCombe," and insert -- Peter M. McCombe, --, therefor.

On the title page, item 75, under "Inventors", in Column 1, Line 7, delete "Anthony J Melkent," and insert -- Anthony J. Melkent, --, therefor.

In the specification

In Column 6, Line 54, delete "end 25." and insert -- end 26. --, therefor.

In Column 9, Line 54, delete "spacer 22" and insert -- spacer 20 --, therefor.

In Column 9, Line 55, delete "spacer 22" and insert -- spacer 20 --, therefor.

In the claims

In Column 12, Line 7, in Claim 13, delete "radius" and insert -- radius is --, therefor.

In Column 13, Line 12, in Claim 19, delete "where" and insert -- wherein --, therefor.

Signed and Sealed this
Fifteenth Day of March, 2016

Michelle K. Lee
*Director of the United States Patent and Trademark Office*